United States Patent [19]
Martin et al.

[11] Patent Number: 5,800,548
[45] Date of Patent: Sep. 1, 1998

[54] DEVICE FOR TRANSVERSE SPINAL CONNECTION

[75] Inventors: Alain Martin, Saint Medard En Jalles, France; Bruno Franck, 4 rue jean Giono, F-87180 Isle, France

[73] Assignees: Bruno Franck, Isle; Brienne Industries, Pessac; Alphamed, Bidardt, all of France

[21] Appl. No.: 811,930

[22] Filed: Mar. 5, 1997

(Under 37 CFR 1.47)

[51] Int. Cl.$^6$ ............................................. A61F 2/44
[52] U.S. Cl. ................................................. 623/17; 606/61
[58] Field of Search .............................. 623/17; 606/61, 606/62, 63, 64, 75

[56] References Cited

U.S. PATENT DOCUMENTS

| | | | |
|---|---|---|---|
| 5,282,801 | 2/1994 | Sherman | 623/17 |
| 5,282,862 | 2/1994 | Baker | 623/17 |
| 5,368,594 | 11/1994 | Martin | 623/17 |

FOREIGN PATENT DOCUMENTS

| | | |
|---|---|---|
| 0 446 092 | 9/1991 | European Pat. Off. . |
| 39 24 050 | 1/1991 | Germany . |

*Primary Examiner*—Michael J. Milano
*Attorney, Agent, or Firm*—Young & Thompson

[57] ABSTRACT

A device for transverse spinal connection, comprises a transverse bar (4) secured to at least one spinal osteosynthesis rod (2) with a connecting/blocking member (5) between the transverse bar and the osteosynthesis rod. The transverse bar and osteosynthesis rod are adapted to be connected to each other in situ by the connection/blocking device which is constituted of a first part (6) in the shape of a jaw (8), provided with a passage (10) for the transverse bar (4) and a blocking screw (22) adapted to project into the passage. The connecting/blocking device also includes a second part (7) in the form of an oppositely directed jaw (18) pivoted on the first part (6). The bar (4) in place in the passage (10) being adapted, during screwing in of the screw (22), to come to bear both against the first part (6) and against the second part (7) and to cause the two jaws (8, 18) to move toward each other.

9 Claims, 3 Drawing Sheets

5,800,548

DEVICE FOR TRANSVERSE SPINAL CONNECTION

This application corresponds to French application 96 03053 of Mar. 5, 1996, the disclosure of which is incorporated herein by reference.

The present invention relates to a device for transverse spinal connection usable in neurosurgery, orthopaedic surgery and more generally in surgery of the spine and adapted to constitute an interconnection in particular between two spinal osteosynthesis rods.

These rods, which are longitudinal rods of circular cross section, are adapted to adapt to the physiological curves of the spine or to reestablish these curves and must most often, after emplacement with the aid of pedicular screws or any other system of posterior securement, and so as to permit good setting and good restraint, be interconnected at one or several places with the help of transverse bars.

The devices of the bar type secured to the interconnection with the restraint rods by means of connection and blocking members, have drawbacks. Certain ones use as connection/blocking members types of collars which must first be threaded on the restraint rods before securement of these latter with the pedicular screws or the like.

This does not facilitate emplacement of the rods and, moreover, once the securement of the rods is effected, the transverse bar or bars cannot be changed as to place because the connection/blocking collars are trapped on the rods. Other devices of the same type comprise connection/blocking members which are not threaded on the restraint rods but connected to these latter, once in place, these members being constituted by two parts which surround the rod.

If this system is more practical and flexible than the preceding one, because it permits the emplacement of a transverse connection bar at various points along the restraint rods after their securement and a change in position if desired, it is however not completely satisfactory.

Thus, although the two parts of the connection/blocking members can be connected to the restraint rods in situ, they however surround completely the rods and, because of this, require local intervention on the vertebrae to free the space necessary to receive said parts, which limits moreover the possibilities of implementation of the transverse bars.

The present invention has precisely for its object to overcome these drawbacks by providing a transverse connection system adaptable directly particularly on spinal osteosynthesis rods in situ, without preliminary intervention to free the space necessary and to permit the emplacement of the transverse bars truly in no matter what position of the restraint rods, of course outside the pedicular screws.

To this end, the invention has for its object a transverse spinal connection device, of the type comprising a transverse bar that can be secured to at least one spinal osteosynthesis rod with a system of connection/blocking between said transverse bar and said osteosynthesis rod, adapted to be connected to this latter in situ, characterized in that said connection/blocking member is constituted:

by a first part in the form of a jaw, provided with a passage for the transverse bar and with a blocking screw or the like adapted to project into said passage, and with a second part in the shape of a counter-jaw articulated on the first part, the bar in place in the passage being adapted, during screwing in of said screw, to come into bearing both against the first part and against the second part and to cause these jaws to approach each other.

According to a preferred embodiment, the jaws are configured so as not to completely surround the osteosynthesis rod, the passage provided in the first part extending substantially orthogonally to the axis of the osteosynthesis rod in position between the jaws, the screw is disposed on the other side of the jaws relative to the transverse bar and the second part is articulated on the first by a fork through which passes said transverse bar.

The shape and dimensions of the passage of the transverse bar in the first part are determined such as to permit said bar to swing multidirectionally so as, on the one hand, to permit the jaws to be spaced apart sufficiently to straddle and grip the osteosynthesis rod, and, on the other hand, to give if desired to the transverse bar a certain angulation relative to the osteosynthesis rod to take account of implementation conditions.

Such a device is positioned substantially instantaneously for example to interconnect two osteosynthesis rods in place, by simple engagement of the device from above each of the rods of the jaws, in open position, to the desired positions, then, once the jaws are in position, screwing the screw which presses on the transverse bar and on the second part/jaw, which approaches the first, gripping the osteosynthesis rod. At the end of screwing, not only the osteosynthesis rod but also the transverse bar are firmly blocked relative to the device.

There is thus obtained a firm and certain mutual blocking between the osteosynthesis rod and the transverse bar.

The unblocking of the device, for example for desired replacement along the osteosynthesis rods, is also quite quick and easy.

The manipulation of this device takes place essentially from top to bottom, the patient lying down, without having to perform surgical intervention nor laterally relative to the rod (vivication of the articulations), nor medially, nor again from above the osteosynthesis rod.

Thus, the shape of the tapered end of the jaws and the fact that these latter leave free the periphery of the osteosynthesis rod turned toward the vertebral column, for example over an extent of the order of a third of this periphery, permits the emplacement of said jaws without a problem, which is to say without having to free a space for this purpose with the help of an instrument.

Other characteristics and advantages will become apparent from the description which follows, of an embodiment of the device of the invention, given by way of example only and with respect to the accompanying drawings, in which.

Figure 1:
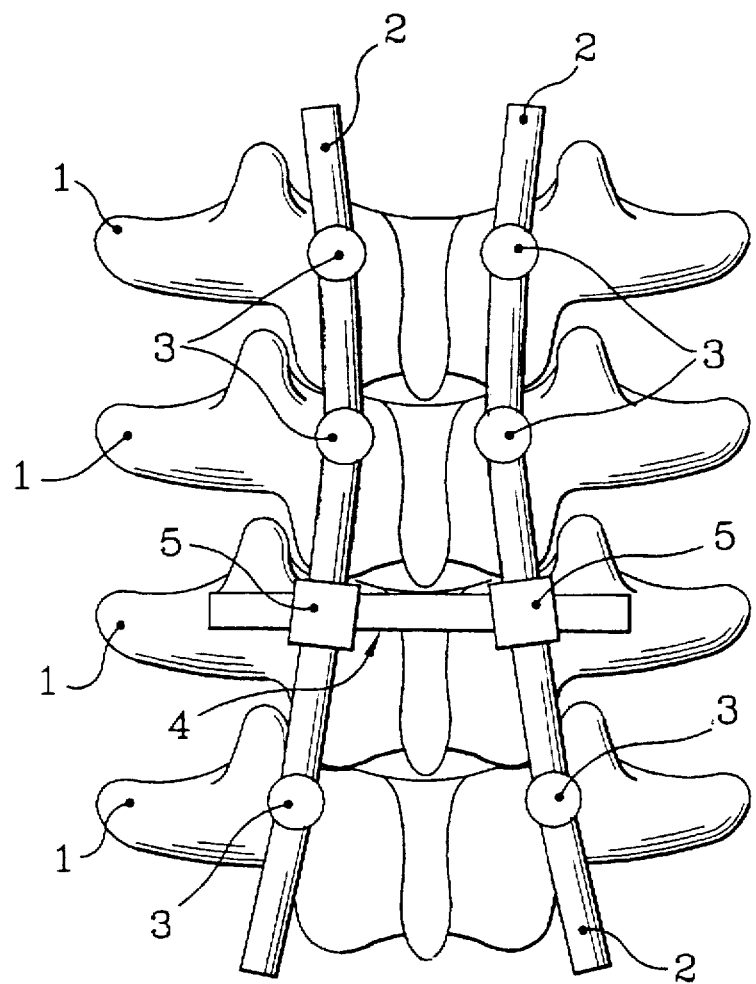
FIG. 1 is a schematic view of a spinal osteosynthesis provided with a transverse connection device according to the invention.

In FIG. 1, there is shown schematically lumbar vertebrae 1 in which two spinal osteosynthesis rods 2 are implanted, in known manner, by means of pedicular screws symbolized at 3.

The two rods 2 are interconnected by a device according to the invention comprising a transverse bar 4 secured to the rods 2 at points of intersection by connecting/blocking means schematically shown at 5.

Figure 2:
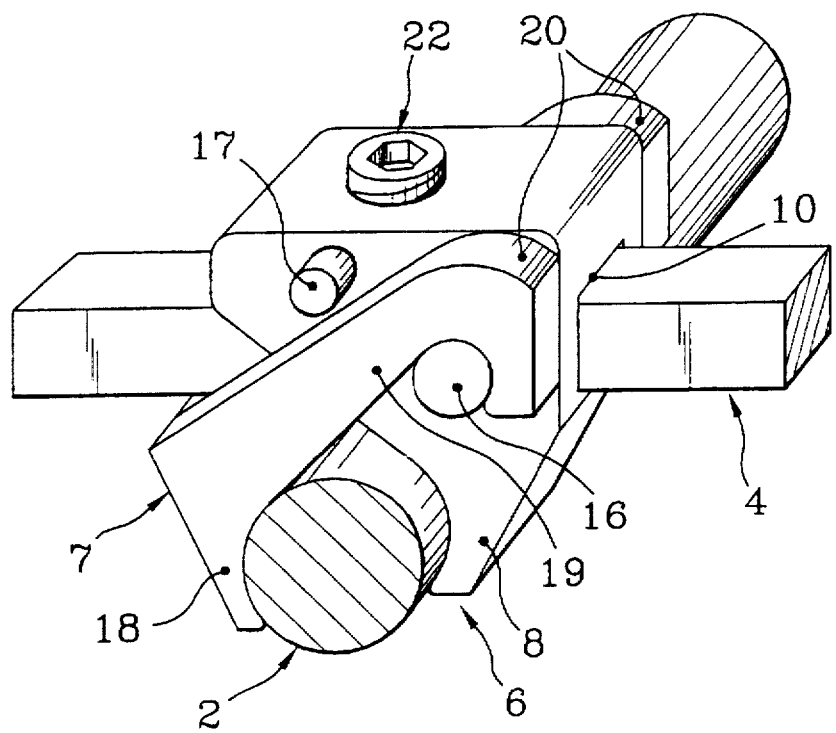
FIG. 2 is a perspective view of a preferred embodiment of the device of the invention.

FIG. 2 shows a preferred embodiment of the device of the invention, which is constituted on the one hand by a transverse connecting bar 4 of rectangular cross section and, on the other hand, a connecting/blocking member 5 between the bar 4 and a cylindrical spinal osteosynthesis rod 2 comprising a first part 6 forming a first jaw and a second part 7 articulated on the part and forming a counter-jaw, the two jaws gripping the osteosynthesis rod 2.

FIGS. 3a to 3c and 4a to 4c show parts 6 and 7 according to FIG. 2.

Figure 3B:
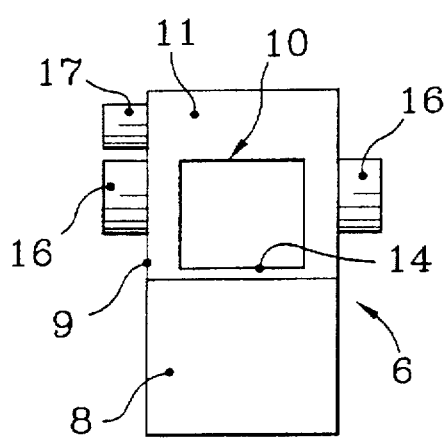
FIGS. 3a to 3c show respectively a view in side elevation, a view from the right and a view from above, of a first part of the device.
Figure 3A:
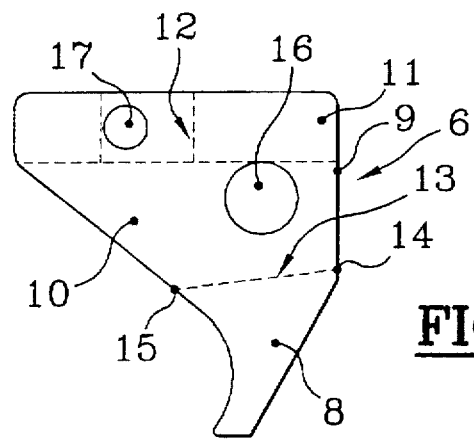
Figure 3C:
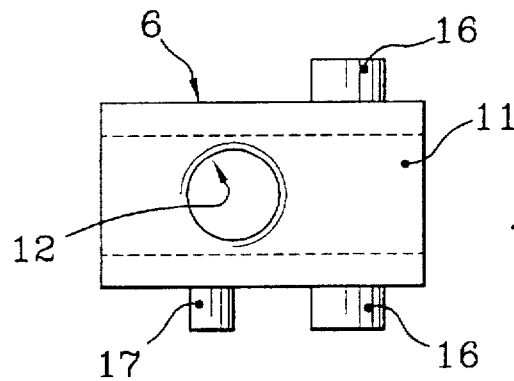

The first part 6 shown by FIGS. 3a to 3c comprises a tapered end forming a jaw 8 with an active cylindrical surface. The jaw 8 is prolonged by a central portion 9 traversed by a passage 10 of rectangular cross section on an axis substantially orthogonal to the axis of the cylinder defining the active face of the jaw 8.

Finally, the central portion 9 is itself prolonged by an end opposed to the jaw 8 and in the shape of a rectangular table 11 in which is pierced a tapped hole 12 opening in said passage 10.

The passage 10 has an inlet section which, as to its height and considering FIG. 3a, increases from right to left such that the bottom 13 of said passage 10 has a high point (ridge 14) at its inlet and a low point 15 at its other end.

On opposite sides of the part 6, at the height of the central portion 9, are provided two pivots 16 on which the part 7 is articulated.

Finally, on one of said flanks is also provided at the height of the table 11 a removable pin 17 for holding the part 7 mounted on the part 6, as will be seen later on.

Figure 4B:
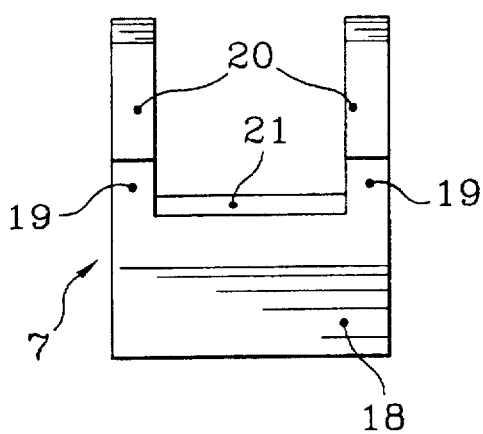
FIGS. 4a to 4c show respectively a view in side elevation, a view from the right and a view from above, of a second part of the device.
Figure 4A:
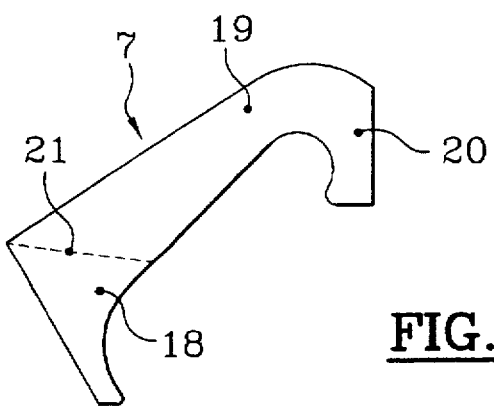
Figure 4C:
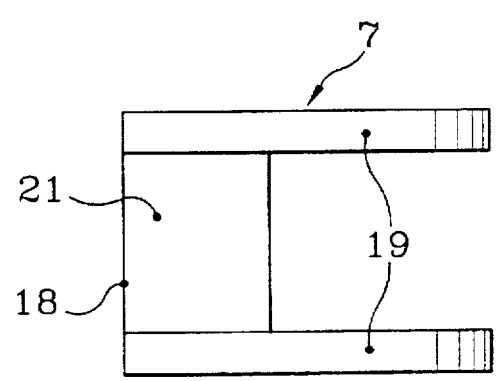

The second part 7 shown in FIGS. 4a to 4c is in the form of a jaw 18 oppositely acting from the jaw 8, the two jaws being substantially symmetrical.

The jaw 18 is prolonged by a fork with two branches 19 whose ends are curved back at 20 so as to swing on the pivots 16 of the part 6. Between the legs 19 extends a surface 21 of the jaw 18 which corresponds to the bottom 13 of the part 6. The parts 6, 7 are mounted and swing as shown in FIG. 2, the pin 17 being inserted in the part 6 after emplacement of the part 7 on the part 6. One of the arms 19 of the part 7 is thus retained trapped between the pin 17 and one of the pivots 16, the part 7 having a certain angular swing to open the pair of jaws 8–18 sufficiently for the passage between them of the rod 2 to be blocked.

Figure 5:
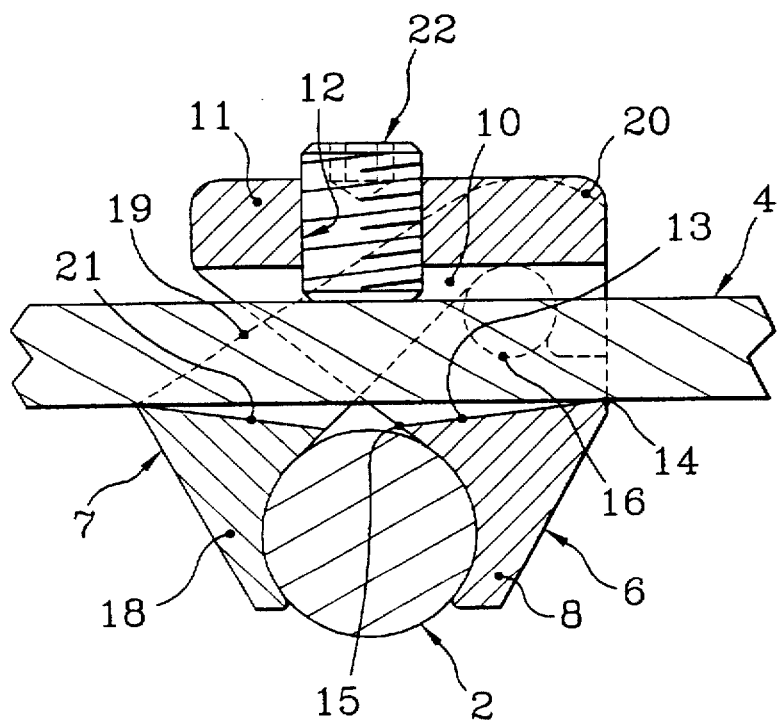
FIG. 5 is a cross-sectional view on the axis of the transverse bar of the device formed by the parts of FIGS. 3a to 3c and 4a to 4c, mounted and in use position.

FIG. 5 shows in cross section the parts 6 and 7 of FIGS. 3a to 3c and 4a to 4c, assembled and mutually blocking the rod 2 and the bar 4.

The manner of use of the device is as follows:

The two parts 6, 7 being assembled and locked by the pin 17, the bar 4 is introduced into the passage 10 and enters the legs 19 of the fork, a screw 22, for example headless and with a hexagonal hollow recess, being inserted in the tapped hole 12 without projecting into the passage 10 so as not to prevent the engagement of the transverse bar 4.

Adjacent the rod 2 at the place where it is desired to block the bar 4, there are jaws 8, 18 against the rod 2. The pressure exerted opens these jaws which then surround the rod 2. It then suffices to screw in the screw 22. This latter projects into the passage 10, bears against the surface that faces the bar 4 which itself swings about an axis parallel to the axis of articulation (pivots 16) of the parts 6, 7, bearing on the input ridge 14.

Swinging the bar 4 to bear on the part 7 between the legs 19 and causing it to pivot such that jaw 18 approaches jaw 8, thus wedges the rod 2.

At the end of screwing, the rod 2 is firmly blocked between the jaws 8, 18 and the bar 4 is firmly blocked between the screw 22 and the part 7.

The height of the passage 10 is substantially greater than the thickness of the bar 4 to permit the part 7 to space itself from the part 6 sufficiently for the free passage of the rod 2 between the jaws 8, 18. The width of the passage 10 is moreover slightly greater than that of the bar 4 so as to permit a certain angular adaptation between the rod 2 and the bar 4. Thus, as shown in FIG. 1, the two osteosynthesis rods 2 are voluntarily disposed out of parallelism such that the transverse bar 4 does not form a right angle with the rods 2.

The device of the invention permits such a mounting, the parts 6, 7 remaining aligned on rods 2, but the bar 4 being adapted slightly to pivot laterally relative to these parts. This avoids having to bend the bar 4 to have a crossing at an accurately right angle with the rods 2.

Unblocking and removal of the device are also rapid and easy because it suffices to unscrew the screw 22 and to pull on the bar 4 or the parts 6, 7 to withdraw the jaws 8, 18.

As can be seen in FIG. 5, a substantial portion (almost one-third in the drawing) of the periphery of the rod 2, on the side of the vertebral column, is disengaged. This, taken with the fact that the shape of the jaws 8, 18 is tapered, permits an emplacement on the rods 2 in no matter what position without having to free the space necessary (vivication of the articulations) in the immediate vicinity of the rods. It is thus that even if the rod 2 is in contact, on its face turned toward the patient, with an osseous tissue, the device of the invention will nevertheless be adapted to be emplaced directly and without preparation.

It is to be noted that the assembled parts 6, 7 could be emplaced on the rod 2 before insertion of the bar 4 into the passage 10.

It is also to be noted that the possibilities of opening the jaws 8, 18 permit the device to adapt to different diameters of osteosynthesis rods (for example, 4, 5 or 6 mm).

The rod 2 and the bar 4, the parts 6, 7 and the screw 22 are of a material suitable for surgical implantation, for example of titanium.

The transverse connection bar 4 has for example a rectangular cross section of 3 mm to 4 mm with rounded edges. The shapes and dimensions of the bar 4 and of the passage 10 of the part 6 can of course vary, the bar 4 being adapted in particular to be square or cylindrical.

Grooves can be provided on the portion of the bar 4 adapted to come into contact with the screw 22.

Finally, the invention is not limited to the embodiment described and shown but on the contrary covers all modifications, particularly as concerns the shape and dimensions of the jaws 8, 18, the manner and means for articulation of the parts 6, 7 with each other, or again the means exerting a pressure on the bar 4 and part 7 to ensure conjointly the blocking relative to the part 6, of the rod 2 and of the bar 4.

What is claimed is:

1. A device for transverse spinal connection, comprising a transverse bar (4) secured to at least one spinal osteosynthesis rod (2) by means of a connection/blocking means (5) between said transverse bar and said osteosynthesis rod, adapted to be connected to the osteosynthesis rod in situ; the improvement wherein said connection/blocking means is constituted:

by a first part (6) in the form of a jaw (8), provided with a passage (10) for the transverse bar (4) and with a blocking screw (22) adapted to project into said passage, and by a second part (7) in the form of an oppositely acting jaw (18) articulated on the first part (6), the bar (4) when in place in the passage (10) being adapted, upon screwing of said screw (22), to come into bearing both against the first part (6) and against the second part (7) and to cause said jaws (8, 18) to come together.

2. Device according to claim 1, wherein said jaws (8, 18) are of tapered shape and arranged so as to leave free a substantial portion of the periphery of the osteosynthesis rod (2).

3. Device according to claim 1, wherein said passage (10) provided in said first part (6) extends substantially orthogonally to the axis of the osteosynthesis rod (2) in position between the jaws (8, 18).

4. Device according to claim 1, wherein said screw (22) is disposed on the other side of the jaws (8, 18) relative to the transverse bar (4) and the second part (7) is articulated on the first part by a fork (19) through which passes said transverse bar (4).

5. Device according to claim 4, wherein said fork (19) ends in two reversely curved ends (20) coacting with two pivots (16) provided on the sides of the first part (6).

6. Device according to claim 5, wherein the angular swinging of the second part (7) relative to the first part (6) is limited by a removable pin (17).

7. Device according to claim 1, wherein the dimensions of said passage (10) are substantially greater than those of the transverse bar (4).

8. Device according to claim 1, wherein said passage (10) is adapted to permit the swinging of said transverse bar (4) within the passage, about an axis parallel to the axis of articulation of said parts (6, 7), under the action of said screw (22).

9. Device according to claim 1, wherein said transverse bar (4) has a rectangular or square cross section.

* * * * *

UNITED STATES PATENT AND TRADEMARK OFFICE
CERTIFICATE OF CORRECTION

PATENT NO. : 5,800,548
DATED : September 1, 1998
INVENTOR(S) : Alain MARTIN et al.

It is certified that error appears in the above-indentified patent and that said Letters Patent is hereby corrected as shown below:

On the title page, insert Item [30] as follows:

--[30] Foreign Application Priority Data
March 5, 1996 [FR] France........96 03053--.

Signed and Sealed this

Second Day of February, 1999

Attest:

Attesting Officer

*Acting Commissioner of Patents and Trademarks*